United States Patent

Giuffre et al.

[11] Patent Number: 5,923,433
[45] Date of Patent: Jul. 13, 1999

[54] OVERMOLDED FLOWTHROUGH TURBIDITY SENSOR

[75] Inventors: Thomas R. Giuffre, Freeport; Bruce B. Figi, Rockford; Sharadkumar D. Patel; Thomas M. Moyer, both of Freeport, all of Ill.

[73] Assignee: Honeywell Inc., Minneapolis, Minn.

[21] Appl. No.: 08/959,412

[22] Filed: Oct. 28, 1997

[51] Int. Cl.⁶ .............................. G01N 21/00; G01N 1/10

[52] U.S. Cl. ............................................ 356/440; 356/246

[58] Field of Search ..................................... 356/246, 436, 356/440–442; 68/12.02

[56] References Cited

U.S. PATENT DOCUMENTS 5,291,626  3/1994  Molnar et al. ......................... 68/12.02
5,446,531  8/1995  Boyer et al. .............................. 356/72

Primary Examiner—Robert H. Kim
Assistant Examiner—Amanda Merlino
Attorney, Agent, or Firm—Roland W. Norris

[57] ABSTRACT

A flow-through visible-light turbidity sensor is constructed from a molded plastic flow tube with an overmolded opaque housing to shield the optical sensing apparatus from ambient light. The housing also secures and covers all electronics for the sensor. The molded parts provide lower cost and less dimensional variation for the sensor as well as the ability to locate conductivity or other physical probe sensor types within the package.

10 Claims, 4 Drawing Sheets

TOP VIEW

OVERMOLDED FLOWTHROUGH TURBIDITY SENSOR

BACKGROUND OF THE INVENTION

1. Field of the Invention

The present invention generally relates to turbidity sensors. The present invention more particularly relates to a turbidity sensor with a tube through which the sensed media/liquid flows and which utilizes light for sensing the turbidity; and which may further contain conductivity sensors or the like for the sensed media.

2. Description of the Prior Art

Turbidity sensors utilizing light to sense the amount of particulates in a solution are known in the art. Reference may be had to U.S. Pat. No. 5,446,531 to Boyer et al. for background discussion of the related art as it might particularly apply to a fluid condition sensor which is placed in, or surrounded by, the liquid or media to be sensed.

Reference may also be had to U.S. Pat. No. 5,291,626 to Molnar et al. for discussion of a turbidity sensor of the visible light, or optical, variety in which the liquid to be sensed flows through a clear tube surrounded by the optical sensing components.

As seen in FIG. 1, a visible light flowthrough turbidity sensor, as currently known, utilizes a casing having first and second halves 11 and 13, respectively, which are opaque and which totally surround a quartz glass media tube 15 which is inserted through an opaque tube 17 contained on a PCB assembly 19 which contains the optical and electronic components required for the output of a turbidity signal. O-rings 21 and 23 are used at each end of the quartz glass media tube 15 to prevent ambient light from leaking into, and the sensed media from leaking out of the media tube.

However, this known arrangement, as seen in FIG. 1, has several disadvantages. First, related to the quartz glass media tube, the glass is expensive, brittle, and is subject to wide dimensional variations among different tubes due to inherent manufacturing tolerances. Therefore, the O-rings are made oversized so that they may account for the size variations within one or several runs of glass tube manufacture. Expense and breakability of the glass are obvious shortcomings in a manufacturing environment. Further, it is very difficult to insert additional probes through the glass wall of the tube in order to contact the media physically. Such probes as temperature or conductivity probes are therefore not easily integrated into this package. Further, anywhere there is an O-ring there is a potential failure point.

It is therefore an object of the present invention to provide a turbidity sensor which overcomes the cited difficulties of the known art and provides for a lower cost turbidity sensor package with additional design freedom for multiple sensing apparatus and which has a lower cost and fewer parts than the known visible light flowthrough turbidity sensor packages.

SUMMARY OF THE INVENTION

The preferred embodiment of the present invention has four basic parts as opposed to the prior art six parts. A molded optically clear media tube for passing the media to be sensed is overmolded with the first half of a sensor casing to seal off light from the tube at two spaced, circumferential areas. The sensor casing is opaque to prevent the entrance of ambient, or noise, light which would interfere with the visible light sensing during turbidity determination operations. The overmolded casing has a void therein for containing within its walls the optical and/or electronic components necessary for sensor operation and output, and for placement of the sensing components around the clear media tube. An opaque casing cover is then mated over the sensing components package to the overmolded casing half to provide a light proof seal over substantially all the sensor package.

Alternatively, dependent on the sensor component desired and molding techniques availed, other constructions and arrangements of the apparatus could be made for effective light sealing of the sensor package. The advantages of the present embodiment include fewer parts, easier construction and assembly, and less expensive parts which are easier to handle and less capable of breaking.

These and other advantages will be more thoroughly realized in connection with the below provided description of the preferred embodiment in conjunction with the accompanying drawings of which like parts are identified by like reference numerals throughout.

BRIEF DESCRIPTION OF THE DRAWINGS

The present invention will be more fully and completely understood from a reading of the Description of the Preferred Embodiment in conjunction with the drawings, in which.

DESCRIPTION OF THE PREFERRED EMBODIMENT

Figure 1:
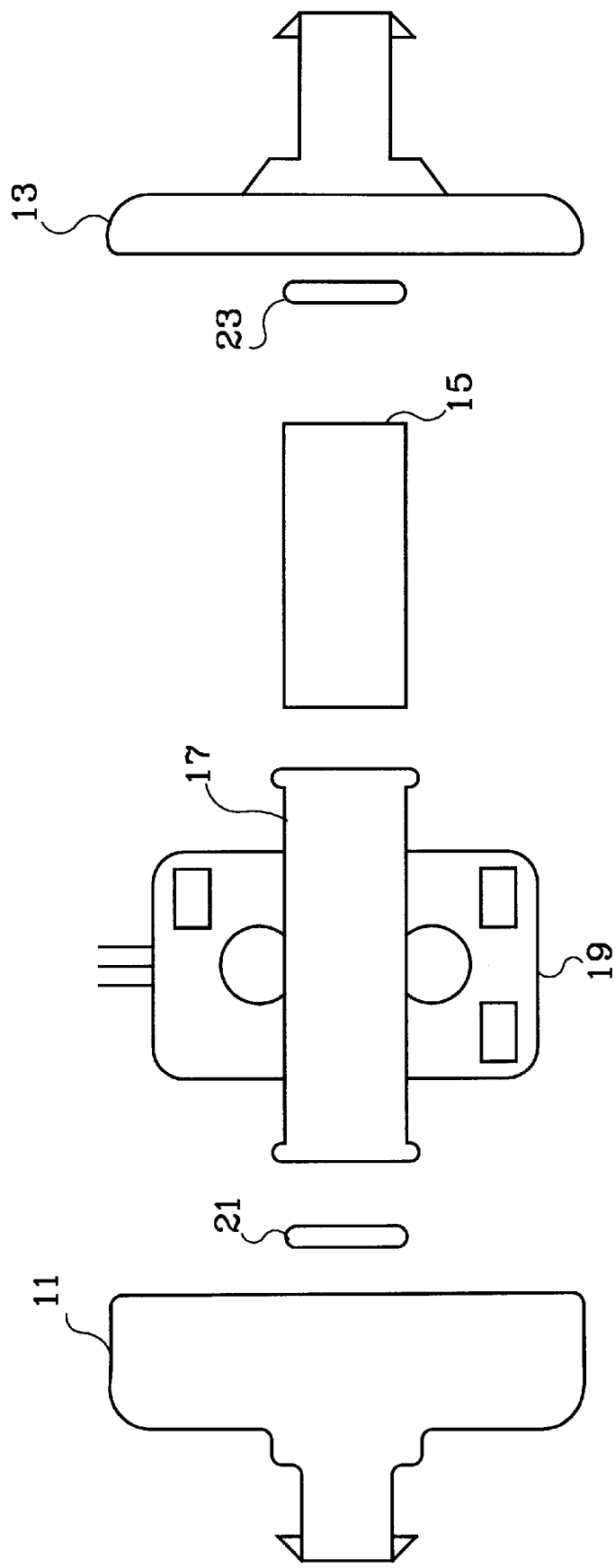
FIG. 1 is an exploded view of a known visible light flowthrough turbidity sensor from the prior art.
Figure 2:
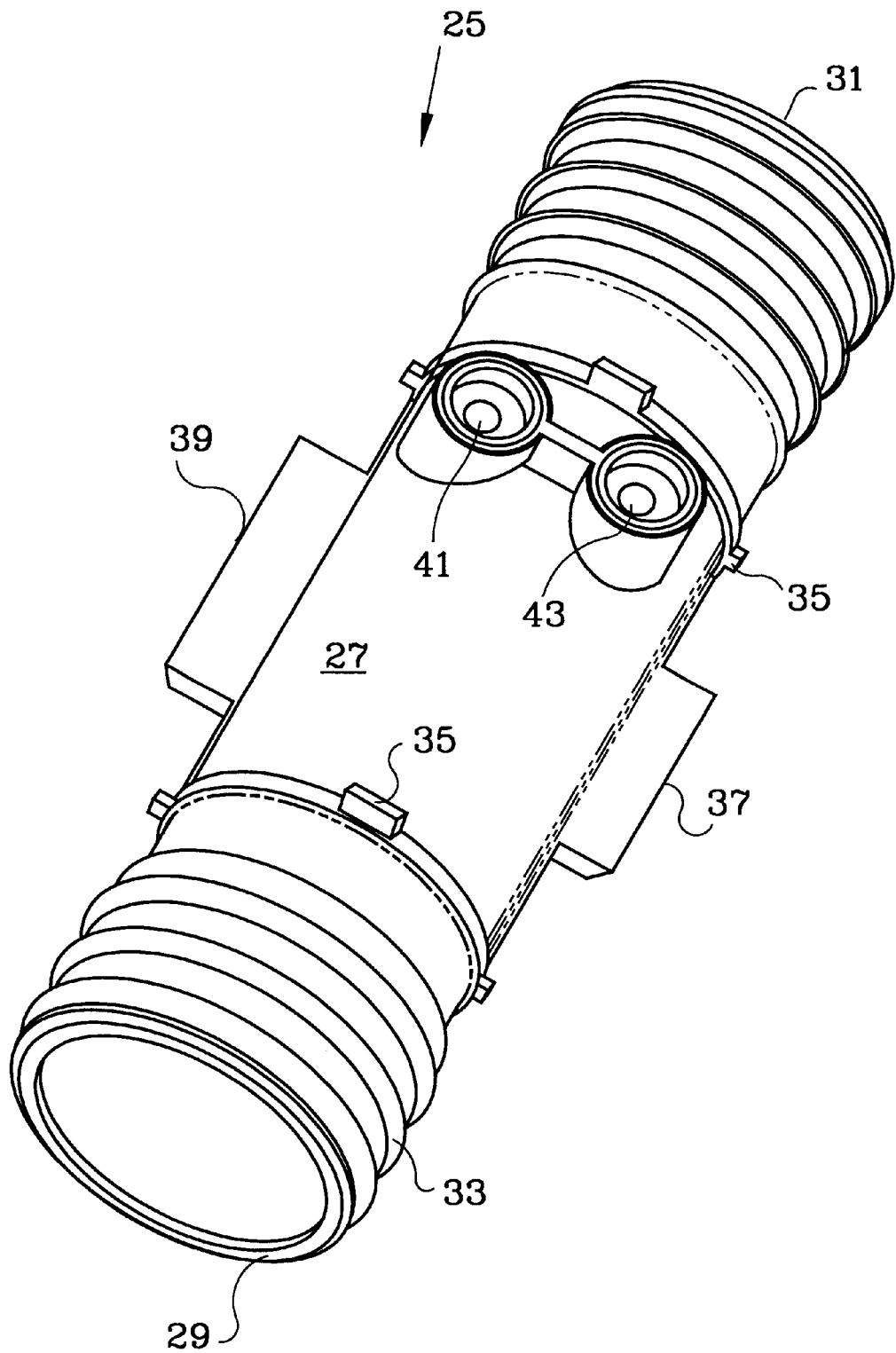
FIG. 2 is a top perspective view of a molded tube according to the preferred embodiment of the present invention.

As seen in FIG. 2, a molded flowtube 25 is constructed and arranged to pass liquid media therethrough for turbidity and other media characteristic sensing as deemed necessary by the application to which the sensor is put. The flowtube 25 has a central optically clear, i.e. tranmissive to the electromagnetic radiation used to sense turbidity, portion 27 which extends circumferentially approximately two thirds of the way around the tube for the transmission and reception of light therethrough. The area of the window may vary according to the optical turbidity sensor requirements of any particular embodiment. Portions of the tube 25 may be made translucent rather than clear depending on the degree of light transmission required. The illustrated embodiment is noted to be a visible light sensor, so the mold for the tube 25 is polished to produce the clear central window 27.

First and second end portions 29 and 31, respectively, are on opposing sides of the axially central window portion 27 and are ridged as at reference numeral 33 in order to accept and secure media transmission lines such as hosing or the like to the flow tube 25. Radial attachment tabs, collectively 35, are provided at the shoulder borders between the end pieces 29, 31 and the central window portion 27. The attachment tabs 35 will be secured to the overmolded opaque casing, as described below, helping to affix and positionally secure the flow tube 25 to the casing. First and second sensor tube tabs, 37 and 39 respectively extend outward from the tube wall at the bottom of the window portion 27. The sensor tube tabs 37 and 39 provide positioning means for the optical sensing apparatus which abut thereto as further explained below.

As further seen in FIG. 2, the preferred embodiment of flow tube 25 has molded therein throughholes 41, 43 for supporting physical characteristic sensing probes, such as temperature or conductivity probes, which need to pass through the tube wall to touch the media flowing therethrough in the interior of the flow tube. Through holes 41, 43 are constructed and arranged to accommodate probes as well as liquid sealing devices such as O-rings or the like as further explained below. The bottom portion of the flow tube 25 may be left translucent rather than clear to minimize mold polishing costs.

The tube 25 is composed of an optically clear plastic or like material which is moldable into the form desired. Particular compositions of the tube may be dictated by different optical or physical characteristics required for the sensing system or the media flowing through the tube and are considered within the ordinary skill of the art.

Figure 3:
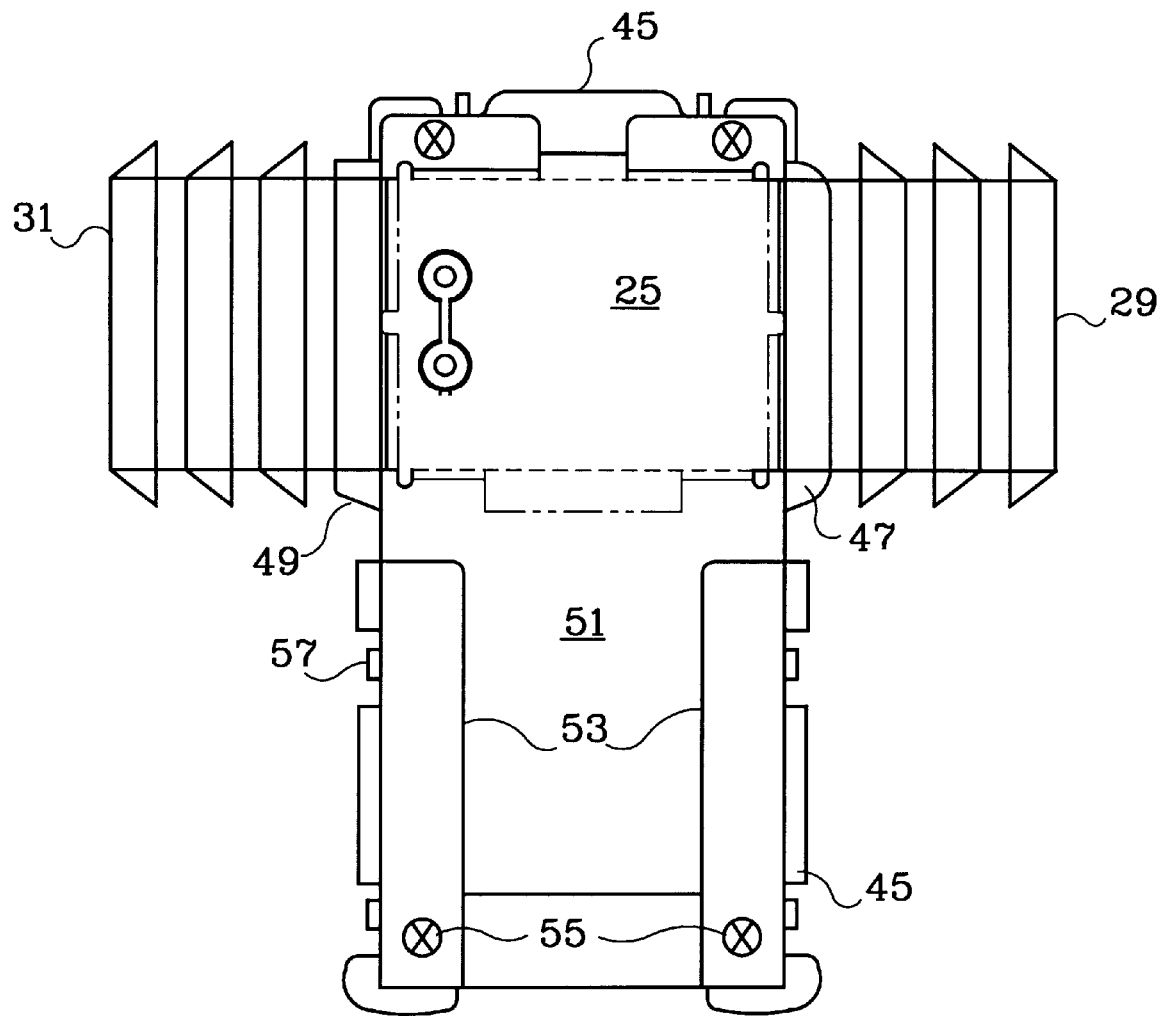
FIGS. 3 and 4 are top and bottom views of the overmolded casing showing the flow tube therein, respectively.
Figure 4:
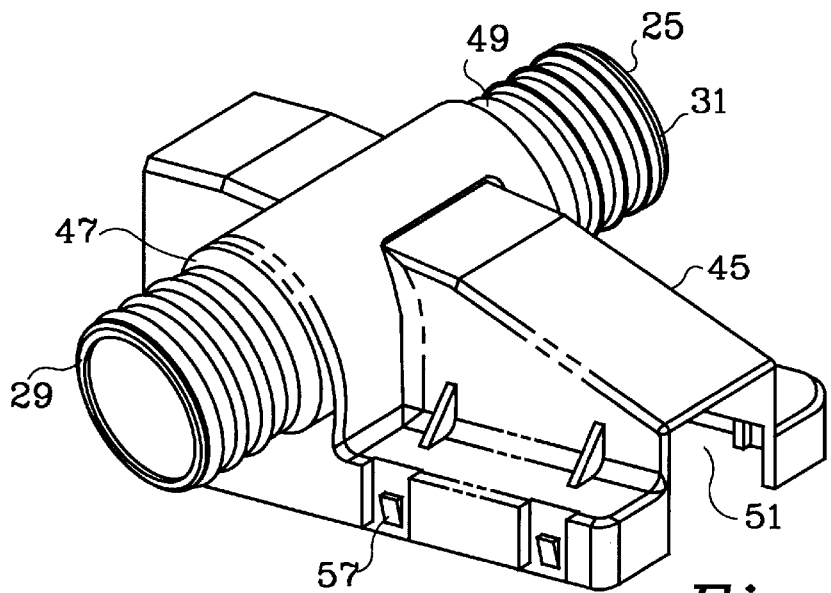

As seen in FIGS. 3 and 4, the overmolded casing 45 substantially surrounds the axially central clear window portion 27 of the tube 25. The overmolded casing 45 is made from an opaque plastic or other such material suitable for circumferentially surrounding the tube 25 at axial locations between the end portions 29, 31 and the clear window 27 of the tube. The molded surround creates extensions 47 and 49 extending from the main side wall of the casing 45. The casing 45 also noncircumferentially surrounds the bottom portion of the tube window section 27 and provides a void or central channel 51 providing room for a sensing components package PCB as further explained below. The extensions 47, 49, when abutted by hosing or other opaque media conduit carrying the media to be sensed, provide a light seal preventing unwanted ambient light from entering the end portions 29, 31 of the molded flow tube 25. The tube end portions could also be made opaque if additional protection against ambient light were desired.

As seen in FIG. 3, formed in the overmolded casing 45 are bosses 53 for the support of the sensing components package (FIG. 5) and capture posts 55 for engaging corresponding holes on the sensing component package for the positional and mechanical securement thereof.

Figure 6:
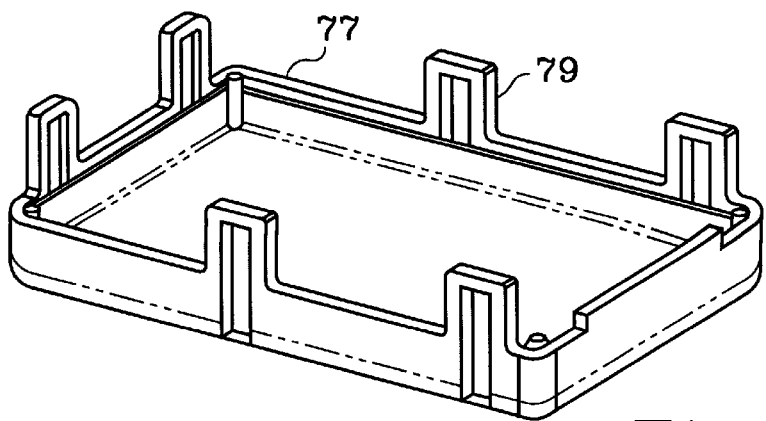
FIG. 6 is a view of the top of the opaque casing cover mateable with the overmolded casing, to complete the ambient light impervious sensor package according to a preferred embodiment of the present invention.

On the outer wall of the overmolded casing 45 are formed protrusions 57 for accepting and retaining attachment loops formed in the top cover (FIG. 6).

Figure 5:
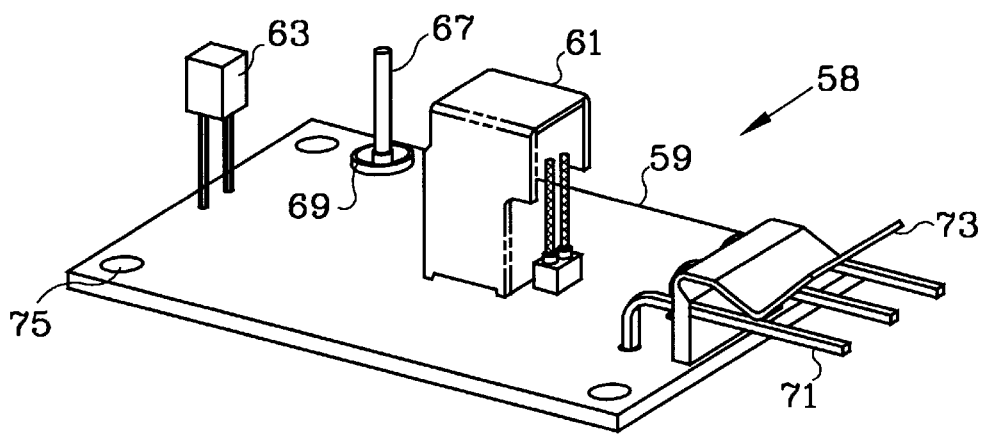
FIG. 5 is a view of a PC board representing the sensing components package of optical and physical sensing apparatus contained within the sensor package.

The sensing components package 58 is seen in FIG. 5. The sensing components package 58 has a PC board 59 supporting a light emitter 61, a transmitted light detector 63 and additional physical probes 67 represented here by a conductivity probe surrounded at its base by an O-ring 69. The light emitter, in situ, abuts second sensor tube tab 39, while the light detector 63 abuts the first sensor tube tab 37. The physical probes 67 fit through through-holes 41 and 43 of the flow tube and are sealed by the O-rings 69 at their base. Other optical or physical sensors might be added as required. Additional electronic components necessary for sensor signal processing would typically be mounted on the PCB 59 but are not shown for the sake of simplicity. Input/output leads 71 provide external electric/electronic connection outside the sensor package. A spring clip 73 for attachment of outside cabling is further provided. Throughholes 75 in the PC board 59 are provided for cooperative engagement with the capture posts 55 of the overmolded casing 45.

It will be appreciated that the present invention will allow a variety of different light, or electromagnetic radiation, sensors as well as physical sensors to be positioned on the sensor package 58 so as to surround or engage the flow tube in order to take a variety of different kinds of measurements on the media flowing therethrough.

FIG. 6 shows the top cover 77 which is used to seal the sensor package when the sensing components package is placed within the overmolded casing. The top cover 77 physically protects the sensor package and prevents additional transmission of ambient light to the visible light sensing area surrounding and including the clear window portion 27 of the flow tube 25. As shown, top cover 77 contains loops 79 extending therefrom to engage overmolded casing protrusions 57 for removable attachment of the top cover. It will of course be appreciated that the top cover may also be attached with adhesives or other suitable means. Alternatives may include molding the top cover to the sensor package or molding the sensor package into a one piece casing.

Thus there has been shown and described a visible light flow-through turbidity sensor having the advantages of low cost multiple sensor access and ease of assembly over those known in the prior art. While a particular embodiment has been shown and described it will of course be appreciated that many other embodiments are within the scope of the present invention as described by the appended claims.

The embodiments of the invention in which an exclusive property or right is claimed are defined as follows:

1. A flowthrough turbidity sensor comprising:
   a) a flow tube having a portion transmissive to a sensing electromagnetic radiation, and means for receiving and outputing a media to be sensed for turbidity;
   b) an opaque casing molded in place around the transmissive portion of the flow tube;
   c) an electromagnetic radiation source for emitting electromagnetic radiation through said tube, said source contained within said opaque casing;
   d) an electromagnetic radiation sensing element positioned to receive said emitted electromagnetic radiation, said element contained within said opaque casing, for outputting a signal based on the amount of electromagnetic radiation received from said electromagnetic radiation source;
   whereby a fluid flowing through said flow tube may have its turbidity sensed by the amount of electromagnetic radiation received by said sensing element.

2. The turbidity sensor according to claim 1:
   wherein the flow tube comprises a molded plastic tube.

3. The turbidity sensor according to claim 1:
   wherein the electromagnetic radiation is visible light.

4. The turbidity sensor according to claim 1:
   wherein the opaque casing contains a void for receiving said emitting source and said sensing element.

5. The turbidity sensor according to claim 4:
   wherein the sensor further comprises a top cover mateable within said opaque casing for covering said void.

6. The turbidity sensor according to claim 1:
   wherein the flow tube contains throughholes for the passage of physical contact sensing probes to the interior of said flow tube.

7. A flow-through turbidity sensor comprising:
a) a molded flow tube having first and second ends and a clear circumferential portion located between the first and second ends thereof, said ends being connectable to a conduit of a fluid to be sensed;
b) an opaque casing molded in place around the flow tube for substantially preventing ambient light from reaching said clear circumferential portion of said tube and having a void therein for containing sensing components for determining the turbidity of the fluid;
c) a sensing components package having light emitting and light receiving means contained within said opaque casing;
   whereby the fluid to be sensed may have its turbidity determined according to the amount of light received by said receiving means after the light has passed through said tube between said light emitting and said light receiving means.

8. The turbidity sensor according to claim 7, wherein:
the sensor further comprises a top cover mateable with said opaque casing for covering said void.

9. The turbidity sensor according to claim 7 wherein:
the flow tube contains through-holes for the passage of physical contact sensing probes to the interior of said flow tube.

10. A visible-light flowthrough turbidity sensor comprising:
a) a molded flow tube having an interior for passing a media to be sensed and having
   1) a central, optically clear portion,
   2) two end portions for connection within a media transmission line,
   3) attachment tabs for helping secure and position an overmolded casing thereto, and
   4) a through-hole molded therein for receiving a sensor probe to the interior of said flow tube;
b) an opaque casing molded to surround a noncircumferential part of said optically clear tube portion and at least a circumferential portion of said tube end portions, the casing having a void for containing sensing components therein and forming an optical sensing area and bosses for the mechanical placement and securing of the sensing components;
c) an opaque casing cover for mating with said casing to help prevent ambient light from entering the optical sensing area;
d) a sensing components package positionable in said opaque casing void and having light emitting and light receiving means positionable about said molded flow tube and other components necessary for generating a turbidity output signal; and
e) wherein said flow tube, casing, casing cover and sensing package are constructed and arranged to make a sensor package substantially impervious to ambient light.

* * * * *